United States Patent
Ortiz et al.

(10) Patent No.: US 8,096,459 B2
(45) Date of Patent: Jan. 17, 2012

(54) SURGICAL STAPLER WITH AN END EFFECTOR SUPPORT

(75) Inventors: Mark S. Ortiz, Milford, OH (US); Michael Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 882 days.

(21) Appl. No.: 11/163,243

(22) Filed: Oct. 11, 2005

(65) Prior Publication Data
US 2007/0083233 A1    Apr. 12, 2007

(51) Int. Cl.
*A61B 17/068* (2006.01)
(52) U.S. Cl. ............... 227/176.1; 227/175.1; 227/19
(58) Field of Classification Search .......... 227/175.1, 227/176.1, 179.1, 180.1, 181.1, 19
See application file for complete search history.

(56) References Cited

U.S. PATENT DOCUMENTS

| | | | | |
|---|---|---|---|---|
| 2,965,900 A | * | 12/1960 | Inokouchi | 227/144 |
| 3,316,914 A | * | 5/1967 | Collito | 606/150 |
| 3,981,308 A | * | 9/1976 | Schlein | 606/205 |
| 4,241,861 A | * | 12/1980 | Fleischer | 227/135 |
| 4,505,414 A | | 3/1985 | Filipi | |
| 4,605,004 A | | 8/1986 | DiGiovanni et al. | |
| 4,754,909 A | | 7/1988 | Barker et al. | |
| 5,047,039 A | | 9/1991 | Avant et al. | |
| 5,100,420 A | * | 3/1992 | Green et al. | 606/143 |
| 5,236,437 A | | 8/1993 | Wilk et al. | |
| 5,236,438 A | | 8/1993 | Wilk | |
| 5,258,008 A | | 11/1993 | Wilk | |
| 5,308,357 A | * | 5/1994 | Lichtman | 606/205 |
| 5,358,506 A | * | 10/1994 | Green et al. | 606/151 |
| 5,376,095 A | * | 12/1994 | Ortiz | 606/143 |
| 5,413,268 A | * | 5/1995 | Green et al. | 227/176.1 |
| 5,425,745 A | * | 6/1995 | Green et al. | 606/219 |
| 5,441,494 A | * | 8/1995 | Ortiz | 606/1 |
| 5,452,832 A | | 9/1995 | Niada | |
| 5,458,279 A | * | 10/1995 | Plyley | 227/176.1 |
| 5,501,251 A | * | 3/1996 | Vader et al. | 140/53 |
| 5,553,765 A | | 9/1996 | Knodel et al. | |
| 5,597,107 A | | 1/1997 | Knodel et al. | |
| 5,630,539 A | * | 5/1997 | Plyley et al. | 227/175.1 |
| 5,637,110 A | | 6/1997 | Pennybacker et al. | |
| 5,673,840 A | | 10/1997 | Schulze et al. | |
| 5,678,748 A | * | 10/1997 | Plyley et al. | 227/175.4 |
| 5,692,668 A | * | 12/1997 | Schulze et al. | 227/175.1 |
| 5,697,432 A | | 12/1997 | Yun et al. | |
| 5,709,680 A | | 1/1998 | Yates et al. | |
| 5,732,872 A | | 3/1998 | Bolduc et al. | |
| 5,769,303 A | | 6/1998 | Knodel et al. | |

(Continued)

FOREIGN PATENT DOCUMENTS
EP    1 400 206 A1    3/2004
(Continued)

*Primary Examiner* — Lindsay Low
(74) *Attorney, Agent, or Firm* — Nutter McClennen & Fish LLP

(57) ABSTRACT

A surgical stapler is provided having a cartridge arm for holding staples, an anvil pivotally connected thereto to deform fired staples from the cartridge arm, and a support for substantially preventing anvil deflection during staple firing to help insure proper staple formation. Some supports allow pivoting between the anvil and cartridge arm when in a first position, but prevent or hinder the pivoting action when in a second position. Supports can also be adapted to contact the anvil at a distal position relative to the pivot point between the anvil and cartridge arm. Exemplary structures of supports embodied as one or more links or as a sleeve are described. Methods of use are also discussed.

25 Claims, 7 Drawing Sheets

U.S. PATENT DOCUMENTS

| | | | |
|---|---|---|---|
| 5,769,848 A | 6/1998 | Wattanasirichaigoon | |
| 5,779,130 A * | 7/1998 | Alesi et al. | 227/176.1 |
| 5,779,131 A | 7/1998 | Knodel et al. | |
| 5,779,132 A | 7/1998 | Knodel et al. | |
| 5,810,855 A | 9/1998 | Rayburn et al. | |
| 5,839,639 A | 11/1998 | Sauer et al. | |
| 5,890,642 A * | 4/1999 | Sato | 227/134 |
| 5,947,363 A | 9/1999 | Bolduc et al. | |
| 5,951,576 A | 9/1999 | Wakabayashi | |
| 6,032,849 A * | 3/2000 | Mastri et al. | 227/176.1 |
| 6,096,037 A | 8/2000 | Mulier et al. | |
| 6,264,084 B1 | 7/2001 | Hayes | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 6,988,649 B2 * | 1/2006 | Shelton et al. | 227/175.2 |
| 7,001,408 B2 | 2/2006 | Knodel et al. | |
| 7,087,071 B2 * | 8/2006 | Nicholas et al. | 606/206 |
| 7,140,528 B2 * | 11/2006 | Shelton, IV | 227/175.4 |
| 2001/0010320 A1 | 8/2001 | Bolduc et al. | |
| 2001/0016749 A1 | 8/2001 | Blatter et al. | |
| 2006/0219752 A1 * | 10/2006 | Arad et al. | 227/176.1 |
| 2007/0265640 A1 * | 11/2007 | Kortenbach et al. | 606/139 |

FOREIGN PATENT DOCUMENTS

| | | |
|---|---|---|
| WO | WO 89/00599 | 1/1989 |
| WO | WO 2004/032754 A2 | 4/2004 |

* cited by examiner

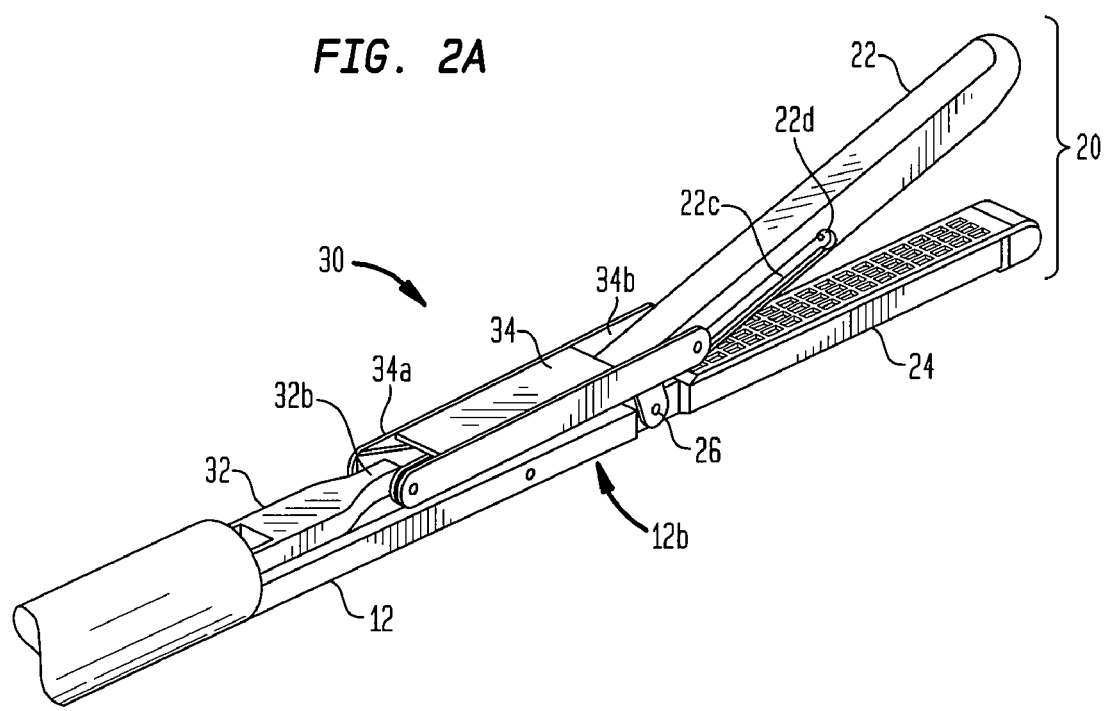

SURGICAL STAPLER WITH AN END EFFECTOR SUPPORT

FIELD OF THE INVENTION

The present invention relates broadly to surgical devices, and in particular to a surgical stapler and/or cutter having a support for an end effector.

BACKGROUND OF THE INVENTION

Endoscopic and laparoscopic surgical instruments are often preferred over traditional open surgical devices since the use of natural orifices (endoscopic) or smaller incisions (laparoscopic) tends to reduce the post-operative recovery time and complications. Consequently, significant development has gone into a range of endoscopic and laparoscopic surgical instruments that are suitable for precise placement of a distal end effector at a desired surgical site. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Typically, endoscopic and laparoscopic surgical staplers have a stapling mechanism, the end effector, which is adapted to fit through a cannula to position the end effector relative to tissue to be stapled. The end effector has a cartridge arm containing a cartridge with staples, and an anvil that is pivotally connected to the cartridge arm. The cartridge arm and anvil each act as a separate jaw to close and hold together the tissue to be stapled. Upon cartridge actuation, staples are driven from the cartridge arm, through the tissue, and against staple-forming grooves formed in the anvil and aligned with the staples of the cartridge arm, thus forming the staples that hold the tissue together.

When a stapler simultaneously fires multiple staples in a linear arrangement, deflection of the anvil can occur. In particular, the force required to drive the staples along with relatively long unsupported length of the anvil can create substantial torque at the anvil's distal end, resulting in deflection. This can result in malformed staples, especially toward the distal end of relatively long end effectors. Since endoscopic or laparoscopic procedures utilize small orifices or access ports, the thickness or outer diameter of the end effector is necessarily limited. Even with the use of very stiff materials for the anvil (e.g., steel or titanium), deflection is still noticeable upon stapler actuation.

Accordingly, a need exists for improved devices and methods for stapling and/or cutting tissue.

BRIEF SUMMARY OF THE INVENTION

The present invention generally provides methods and devices for supporting an anvil on a surgical stapler and/or cutter. In one embodiment the surgical stapler can include an end effector having a cartridge arm to hold one or more staples, and an anvil pivotally coupled to the cartridge arm and effective to deform staples. The device can also include a support adapted to contact the end effector and reduce deflection of the anvil when one or more staples are driven from the cartridge arm and deformed against the anvil. In an exemplary embodiment, the cartridge arm can be adapted to hold a plurality of staples in at least one linear row. The end effector and support can also, in other embodiments, have a maximum outer diameter that is less than about 16 mm when the support is in a collapsed position to allow the end effector to fit within small orifices or cannulas.

The support can have a variety of configurations, but in one embodiment it can be adapted to contact the anvil at a location distal to the pivot point. For example, the support can be slidably coupled to the anvil, and movable between a proximal position in which the anvil can move about the pivot point, and a distal position in which the support prevents the anvil from moving about the pivot point. In an exemplary embodiment, the support can include at least two linkages pivotally coupled to one another, with one of the linkages being slidably coupled to the anvil. In particular, the support can include a distal linkage slidably coupled to the anvil, a proximal linkage pivotally coupled at one end to the distal linkage and at an opposite end to an elongate shaft extending proximally from the cartridge arm, and a middle-linkage pivotally coupled at one end to the elongate shaft and pivotally coupled at an opposite end to the distal linkage and the proximal linkage. In another embodiment, the support can be in the form of a sleeve that is movable between a first position in which the anvil is pivotable relative to the cartridge arm and a second position in which the anvil is prevented from pivoting relative to the cartridge arm. In other embodiments, the device can include a stop member for limiting distal movement of the support. For example, the anvil can include at least one elongate slot for slidably receiving at least one pin member formed on the support. The slot can terminate at a substantial mid-portion of the anvil to limit distal movement of the support.

Exemplary methods for stapling tissue are also provided. In one embodiment, the method can include positioning tissue between a cartridge arm and an anvil of a surgical stapler, and advancing a support relative to the anvil to prevent deflection of the anvil relative to the cartridge arm when one or more staples are driven from the cartridge, through tissue positioned between the anvil and the cartridge arm, and are deformed against the anvil to staple the tissue.

BRIEF DESCRIPTION OF THE DRAWINGS

The invention will be more fully understood from the following detailed description taken in conjunction with the accompanying drawings, in which:

FIG. 2A is a perspective view of the end effector of the surgical stapler of FIG. 1, showing one embodiment of a support in a collapsed position, and the anvil pivoted away from the cartridge arm;

DETAILED DESCRIPTION OF THE INVENTION

In general, a surgical stapler and/or cutter is provided having an end effector for delivering staples to tissue, and a support for preventing deflection of the end effector. In particular, the end effector can include a cartridge arm adapted to hold staples, and an anvil pivotally coupled to the cartridge arm and adapted to deform staples driven from the cartridge arm. The support can be coupled to the end effector and it can be movable between a first, collapsed position in which the anvil arm can pivot relative to the cartridge arm, and a second, extended position in which the support engages the anvil to substantially limit deflection of the anvil when one or more staples are driven from the cartridge arm and deformed against the anvil. The support is particularly effective for use with linear surgical staplers and/or cutters having a relatively long end effector for delivering one or more linear rows or lines of staples, as the support can substantially prevent deflection of a distal end of the anvil during application of long lines of staples. For example, the surgical stapler can have an end effector that has a length that is in the range of about 60 mm to 90 mm. The support is also particularly effective for use in endoscopic and laparoscopic procedures, as the support can be capable of collapsing to allow the end effector and support to be introduced through natural orifices (e.g., the throat) or through small access ports, such as cannulas or other small pathways. For example, in an exemplary embodiment the end effector and support can have a maximum outer diameter that is less than about 16 mm when the support is in a collapsed position to allow the support to be inserted through pathways having a diameter of about 16 mm or less. A person skilled in the art will appreciate that the support can be used with a variety of fastener delivery devices, and that the linear stapler disclosed herein is merely shown for reference purposes.

Figure 1:
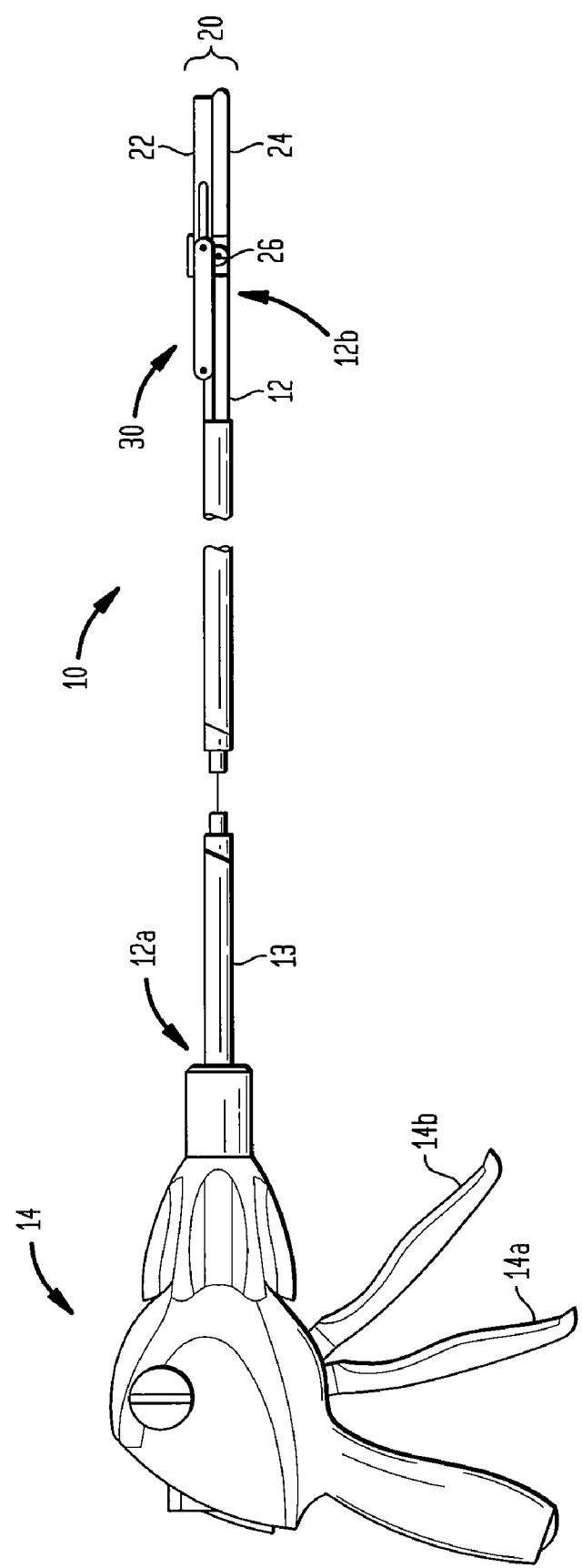
FIG. 1 is a side view of a surgical stapler according to one embodiment of the invention.

FIG. 1 illustrates one exemplary embodiment of a surgical stapler 10 having a support 30 for limiting or preventing deflection of an anvil. As shown, the device 10 generally includes a handle 14 having an elongate shaft 12 extending therefrom, and including proximal and distal ends 12a, 12b. A shaft housing 13 is shown disposed over a portion of the elongate shaft 12. A staple applying assembly or end effector 20 is formed on the distal end 12b of the elongate shaft 12. The end effector 20 includes opposed arms, referred to as a cartridge arm 24 and an anvil 22, that are pivotally coupled to one another at their proximal ends by a pivot point 26, and that are adapted to receive tissue therebetween. The cartridge arm 24 is adapted to contain a staple cartridge having multiple staples disposed therein and configured to be driven into tissue, and the anvil 22 includes a plurality of grooves formed therein for deforming the staples. The device 10 can also include one or more triggers coupled thereto for actuating the end effector 20, e.g., opening and closing opposed jaws of the end effector, and/or driving a cutting blade through the end effector 20. FIG. 1 illustrates a first trigger 14a movably coupled to the handle 14 for closing the opposed jaws of the end effector 20. The handle 14 also includes a second trigger 14b movably coupled thereto for firing the staple cartridge to deliver one or more staples into tissue. The second trigger 14b can also be effective to advance a blade distally through the staple cartridge to cut stapled tissue. While two triggers 14a, 14b are shown, the handle 14 can additionally or alternatively include other actuation mechanisms, such as a rotatable knob, lever, sliding knob, etc. for actuating the end effector 20. A person skilled in the art will appreciate that the device can include a variety of other features not disclosed herein. For example, the device can include an articulation joint formed between the elongate shaft 12 and the end effector 20 for allowing angular movement of the end effector 20 relative to the elongate shaft 12. A trigger or other mechanism can be provided on the handle for angularly adjusting the end effector 20.

Figure 2B:
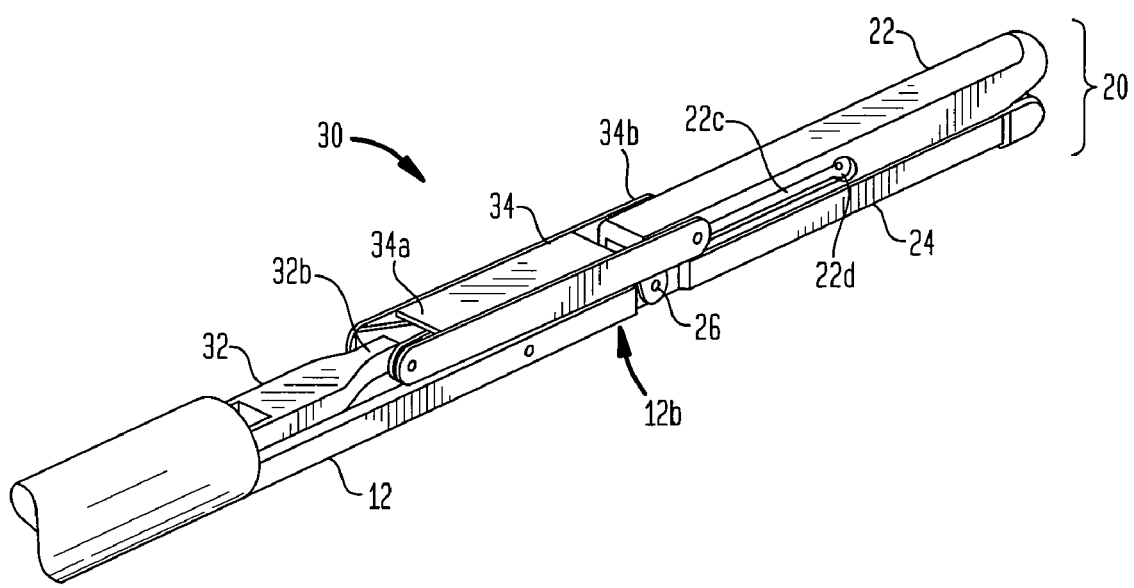
FIG. 2B is a perspective view of the end effector of FIG. 2A, showing the support in a collapsed position, and the anvil and cartridge arm pivoted together.
Figure 2C:
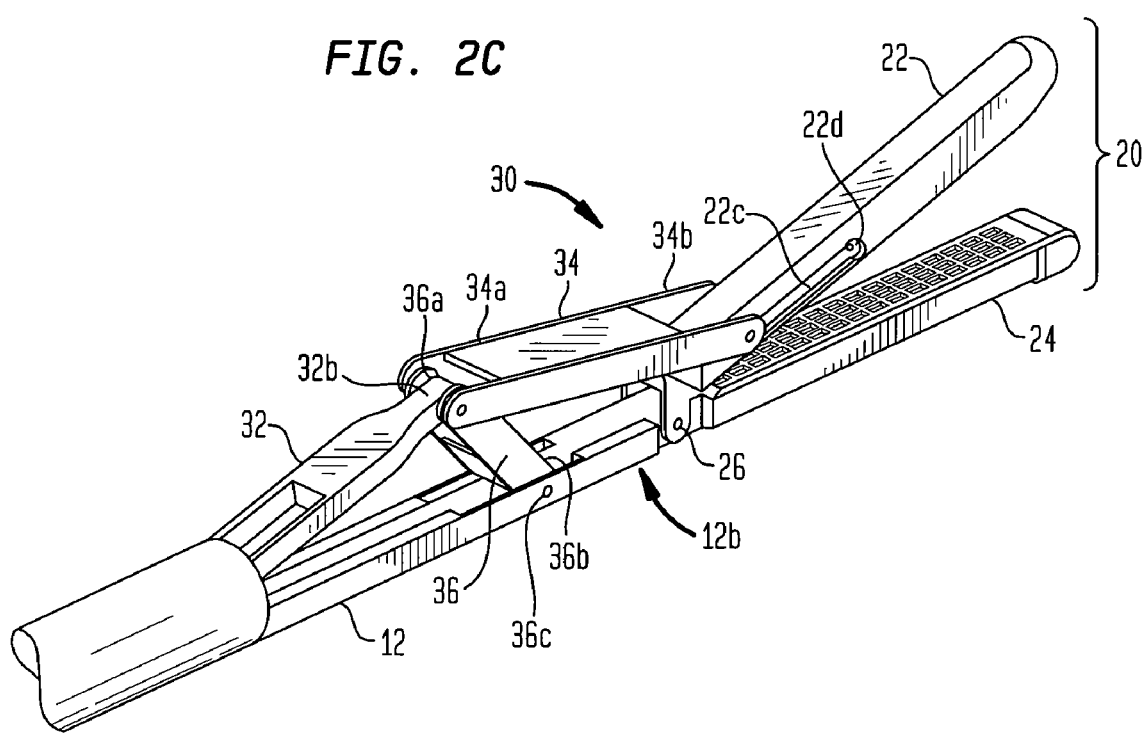
FIG. 2C is a perspective view of an end effector of FIG. 2A, showing the support in a partially extended position relative to the anvil.
Figure 2D:
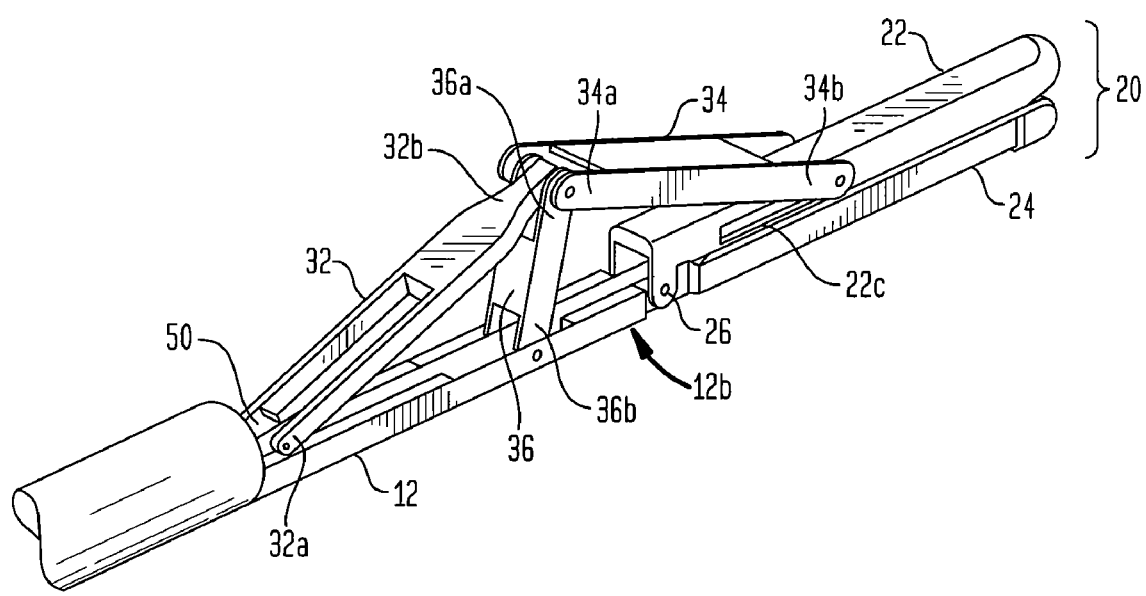
FIG. 2D is a perspective view of the end effector of FIG. 2A, showing the support in a fully extended position to prevent deflection of the anvil.

The support 30 is shown in more detail in FIGS. 2A-2D. As shown, the support 30 is in the form of a linkage assembly that is movably coupled between the elongate shaft 12 and the anvil 22. In particular, the support 30 includes a proximal linkage 32, a distal linkage 34, and a middle linkage 36 which are pivotally coupled to one another and which are movable relative to the elongate shaft 12 and end effector 20. The proximal linkage 32 has a proximal end 32a (FIG. 2D) that is pivotally and slidably coupled to a portion of the elongate shaft 12, and a distal end 32b that is pivotally coupled to a proximal end 34a of the distal linkage 34. The distal linkage 34 extends distally from the distal end 32b of the proximal linkage 32, and it includes a distal end 34b that is pivotally and slidably coupled to the anvil 22. The sliding and pivoting connection between the proximal end 32a of the proximal linkage 32 and the elongate shaft 12b, and between the distal end 34b of the distal linkage 34 and the anvil 22, can be formed using a variety of techniques. For example, the proximal linkage 32 can be coupled to a portion of the elongate shaft 12 that slides, e.g., a sliding push rod 50 (FIG. 2D), and that allows pivotal movement of the proximal linkage 32 relative thereto. The distal linkage 34 can include a pin member that slides within a slot 22c formed in the anvil, and that allows pivotal movement of the distal linkage 34 relative to the anvil 22. As indicated above, the support 30 can also include a middle linkage 36. As shown in FIGS. 2C and 2D, the middle linkage 36 is pivotally coupled at a first end 36a to the distal end 32b of the proximal linkage 32 and to the proximal end 34a of the distal linkage 34, such that all three links 32, 34, 36 are pivotally coupled to one another at a mid-portion of the support 30. The second end 36b of the middle linkage 36 is pivotally coupled to the elongate shaft 12 at a fixed pivot point 36c, such that the middle linkage 36 cannot slide relative to the elongate shaft 12.

In use, the connection between linkages 32, 34, 36 allow the support 30 to move between a proximal, collapsed position in which the anvil 22 can pivot relative to the cartridge arm 24, and a distal, extended position in which the support 30 is effective to limit or prevent deflection of the anvil 22 when one or more staples are driven from the cartridge arm 24 and deformed against the anvil 22. The proximal, collapsed position in shown in FIGS. 2A and 2B, and as shown the linkages 32, 34, 36 are substantially axially aligned with the end effector 20 such that the maximum outer diameter of the elongate shaft 12, end effector 20, and support 30 is substantially constant along a length thereof to allow the distal portion of the device 10 to be introduced through a small pathway, e.g., 16 mm or less in diameter. In particular, the proximal linkage 32 is fully retracted in a proximal direction, e.g., using a trigger or other mechanism formed on the handle of the stapler as will be discussed in more detail below, to pull the distal linkage 34 in a proximal direction such that the distal end 34b of the distal linkage 34 is in a proximal-most position relative to the anvil 22. Proximal retraction of the proximal linkage 32 also pivots the first end 36a of the middle linkage 36 (not shown in FIGS. 2A and 2B) in a proximal direction, such that the middle linkage 36 is received within an opening formed in the elongate shaft 12. In this position, the anvil 22 is free to open and close relative to the cartridge arm 24. FIG. 2A illustrates the anvil 22 in an open position for receiving tissue therebetween, and FIG. 2B illustrates the anvil 22 in a closed position for engaging tissue therebetween. A separate closure mechanism can be used to move the anvil 22 to the closed position, shown in FIG. 2B, or alternatively the support 30 can be used to urge the anvil 22 toward the cartridge arm 24 when the support 30 is moved to the distal, extended position.

The support 30 is shown in the distal, extended position in FIGS. 2C and 2D. As shown, the proximal linkage 32 is advanced, e.g., using a trigger or other mechanism formed on the handle of the stapler as will be discussed in more detail below, in a distal direction toward the end effector 20. The distal movement of the proximal linkage 32 will cause the first end 36a of the middle linkage 36 to pivot about the fixed pivot point 36c formed between the second end 36b of the middle linkage 36 and the elongate shaft 12. As the first end 36a of the middle linkage 36 moves away from the elongate shaft 12 and pivots about the fixed pivot point 36c, the proximal end 34a of the distal linkage 34 will likewise move away from, i.e., rotate relative to, the elongate shaft 12, and the distal end 34b of the distal linkage 34 will slide distally within the elongate slot 22c formed in the anvil 22. When the distal linkage 34 reaches a distal-most position, the force imparted to the proximal linkage 32 no longer advances the distal linkage 34 but rather results in a downward force applied by the distal linkage 34 to the anvil 22 to limit or prevent deflection of the anvil 22 relative to the cartridge arm 24 when staples are being driven from the cartridge arm 24 against the anvil 22.

While the support 30 can engage any portion of the anvil 22, in an exemplary embodiment, the support 30 can be adapted to engage a substantial mid-portion of the anvil 22. Such a configuration can ensure that the distal linkage 34 applies a downward force on the anvil 22, which can optionally be effective to move the anvil to the closed position. Engagement of the mid-portion of the anvil 22 can be achieved using, for example, a stop member to limit distal movement of the support 30 relative to the anvil 22. In the embodiment shown in FIGS. 2C and 2D, an endpoint 22d of the elongate slot 22c formed in the anvil 22 functions as a stop member, as the slot 22c terminates proximal to the distal-most end of the anvil 22. Thus, the endpoint 22d will prevent the distal linkage 34 from sliding distally beyond the distal-most end of the slot 22c, thereby causing the distal linkage 34 to engage the mid-portion of the anvil 22. The endpoint of the slot can also be adjustable using a movable stop pin. The slot can include a number of positions in which a stop pin can be inserted, and the position of the stop pin can determine the extent to which the distal linkage can slide toward the distal end of the anvil before no further sliding can occur. A person skilled in the art will appreciate that a variety of other techniques can be used to create stops or other mechanisms that limit distal movement of the support.

As previously indicated, a variety of techniques can be used to move the support 30 between the proximal and distal positions. For example, in one embodiment the proximal linkage can be pivotally coupled to a push rod 50 (FIG. 2D) extending through the elongate shaft 12 and adapted to slidably move relative to the elongate shaft 12 to advance and retract the proximal linkage 32, thereby moving the support 30 between the proximal and distal positions. A lever, trigger, or other mechanism formed on the handle of the device can be provided for effecting movement of the pusher rod 50. A person skilled in the art will appreciate that movement of the support and/or the pivoting of the anvil and cartridge arm can be accomplished simultaneously or independent of one another, and independent of firing the staples from the cartridge arm 34.

Figure 3A:
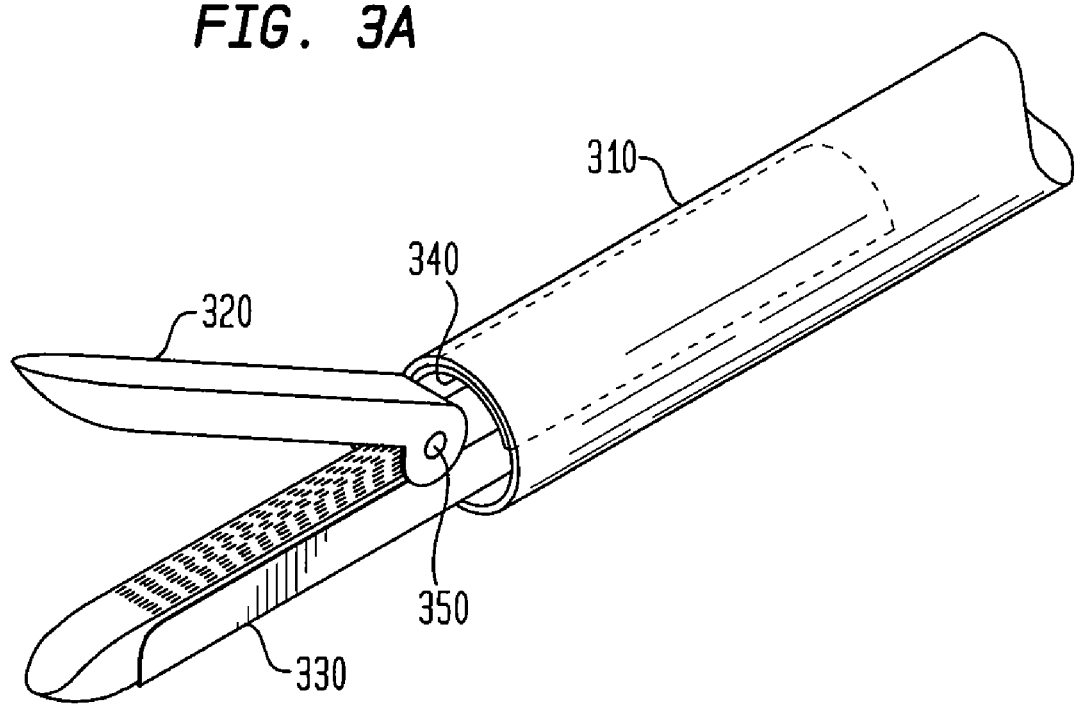
FIG. 3A is a perspective view of another embodiment of an end effector of a surgical stapler, having an anvil pivotally coupled to a cartridge arm, and a support sleeve in a proximal position to allow the anvil to pivot away from the cartridge arm.
Figure 3B:
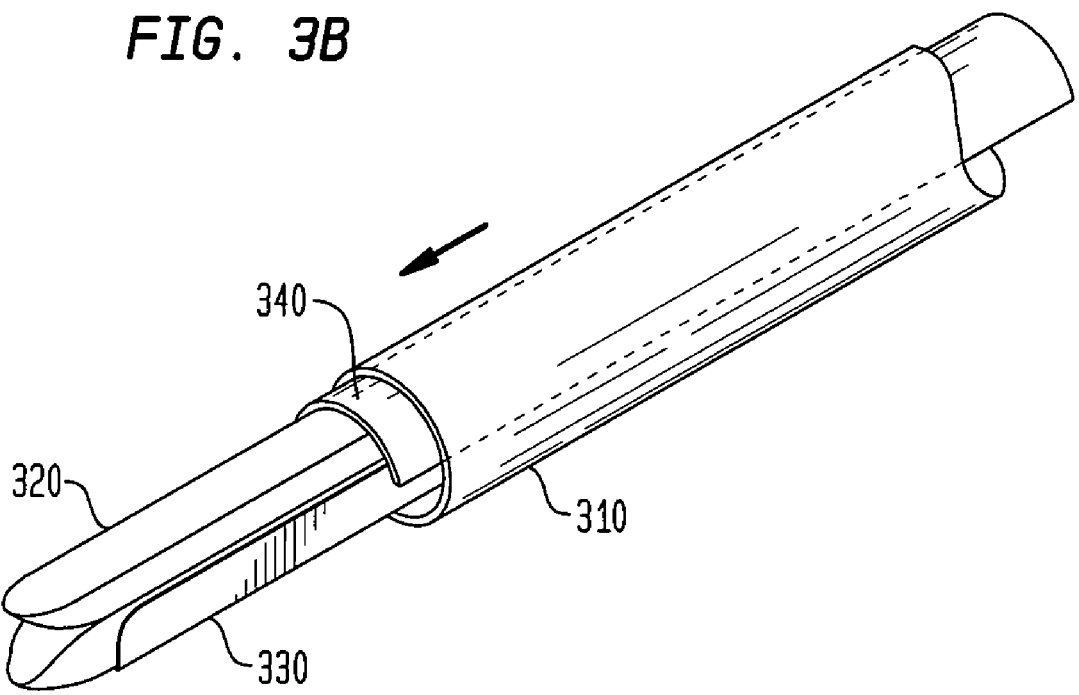
FIG. 3B is a perspective view of the end effector of FIG. 3A, showing the anvil and cartridge arm pivoted toward one another, and the support sleeve advanced toward a distal position to hinder movement of the anvil.
Figure 3C:
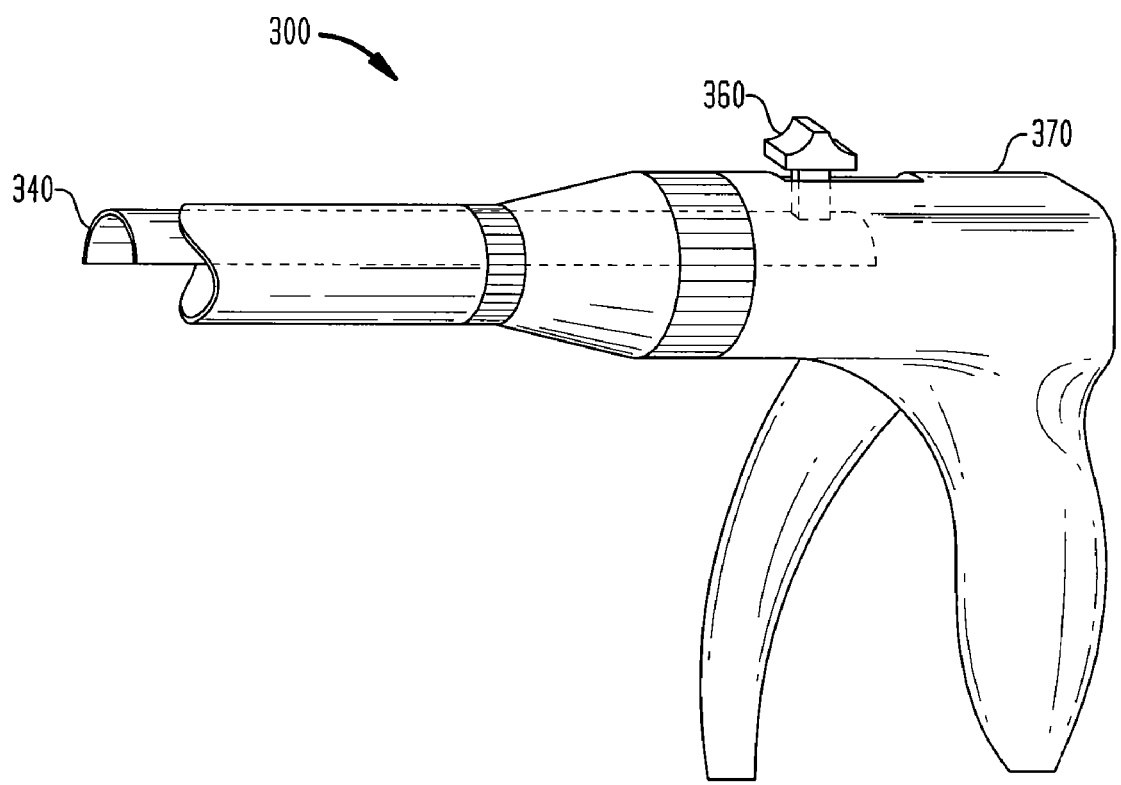
FIG. 3C is a perspective view of a handle portion of the surgical stapler shown in FIG. 3A, showing a lever for moving the support sleeve between the proximal and distal positions.

The support can also have a variety of other configurations to prevent deflection of an anvil on a surgical stapler. In another embodiment, as shown in FIGS. 3A-3C, the support can be in the form of a sleeve that is moveable between a first position and a second position relative to an end effector. As shown, the surgical stapler 300 generally includes an elongate shaft 310 having an end effector formed on a distal end thereof and including an anvil 320 and a cartridge arm 330 pivotally coupled thereto. A sleeve 340 is slidably disposed within the outer housing of the elongate shaft 310, and it is movable between a proximal, retracted position (shown in FIG. 3A) and a distal, extended position (shown in FIG. 3B). The sleeve 340 can have a variety of shapes and sizes, and it can be substantially tubular or, as shown in FIGS. 3A and 3B, it can have a generally elongate shape with a substantially semi-circular cross-section. When the sleeve 340 is in the proximal position, as shown in FIG. 3A, the sleeve 340 is fully retracted relative to the anvil 320 such that it allows the anvil 320 to pivot relative to the cartridge arm 330. When the sleeve 340 is advanced to distal position, the sleeve 340 slides over and contacts the anvil 320 at a location distal to the pivot point 350, thereby hindering or preventing pivotal movement between the anvil 320 relative to the cartridge arm 330. Accordingly, when a staple is fired, the sleeve 340 limits or prevents deflection of the anvil 320.

As with the embodiment shown in FIGS. 2A-2D, movement of the support sleeve 340 can be achieved in a variety of manners. In one embodiment, as shown in FIG. 3C, the handle 370 of the device 300 includes a slide button 360 formed thereon and coupled to a proximal end of the sleeve 340. Thus, movement of the slide button 360 between proximal and distal positions is effective to move the sleeve 340 between proximal and distal positions.

A person skilled in the art will appreciate that the sleeve can have a variety of other configurations, and it does not need to move between a retracted and extended position. For example, a sleeve can be rotatable between a first position in which the sleeve is adjacent to the cartridge arm and allows pivoting of the anvil and cartridge arm, and a second position in which the sleeve is adjacent to the anvil and limits or prevents anvil pivoting with respect to the cartridge arm.

Exemplary methods for stapling tissue are also provided. In one exemplary embodiment, the method can include introducing an end effector of a surgical stapler into a surgical site. The end effector can be inserted endoscopically through a natural orifice, or it can be introduced laparoscopically through a small incision or access port, such as a cannula. The end effector is preferably introduced with the support in a retracted position in which the outer diameter of the elongate shaft of the device is at its smallest or kept to a minimum. For example, with regard to the device 10 shown in FIGS. 2A-2D, the support 30 is preferably introduced in a proximal, collapsed position. With regard to the embodiment shown in FIGS. 3A-3C, the support sleeve 340 can be introduced in either position, as the sleeve 340 does not increase an outer diameter of the device.

Once the end effector is positioned adjacent to tissue to be stapled, anvil and cartridge arm are manipulated to position the tissue therebetween. The anvil is then pivoted toward the cartridge arm, e.g., using the support or using a separate closure mechanism, to engage the tissue between the anvil and cartridge arm. If the support is not used to close the anvil, the support can then be advanced to hinder or prevent movement of the anvil relative to the cartridge arm. The tissue can optionally be squeezed for a period of time to induce "milking" of the tissue, and then the end effector can be actuated to drive staples from the cartridge arm, through the tissue between the anvil and cartridge arm, and against the anvil. The staples will deform against the anvil, and the support will prevent deflection of the anvil.

One skilled in the art will appreciate further features and advantages of the invention based on the above-described embodiments. Accordingly, the invention is not to be limited by what has been particularly shown and described, except as indicated by the appended claims.

What is claimed is:

1. A surgical stapler, comprising:
    an end effector having a cartridge arm for holding at least one staple, and an anvil pivotally coupled to the cartridge arm and effective to deform the at least one staple; and
    a support coupled to the end effector, the support having a distal end movable between a proximal-most position in which the anvil and cartridge arm can pivot between open-most and closed-most positions, and a distal-most position in which the distal end of the support engages at least at a mid-portion of the end effector to prevent deflection of the anvil when at least one staple is driven from the cartridge arm and deformed against the anvil.

2. The surgical stapler of claim 1, wherein the support is axially aligned with the end effector when the distal end of the support is in the proximal-most position, and wherein the support extends substantially transverse to the end effector when the distal end of the support is in the distal-most position.

3. The surgical stapler of claim 1, wherein the support comprises a linkage slidably coupled to the anvil.

4. The surgical stapler of claim 3, wherein the linkage includes a proximal linkage pivotally coupled to an elongate shaft that extends proximally from the end effector, and a distal linkage pivotally coupled at one end to the proximal linkage and at an opposite end to the anvil.

5. The surgical stapler of claim 4, wherein the distal linkage is coupled to the anvil at a position distal to a pivot joint formed between the anvil and the cartridge arm.

6. The surgical stapler of claim 1, further comprising an actuator coupled to the end effector and adapted to urge the anvil toward the cartridge arm.

7. The surgical stapler of claim 1, wherein the support is adapted to urge the anvil toward the cartridge arm.

8. A surgical stapler, comprising:
    a cartridge arm adapted to hold a plurality of staples;
    an anvil having proximal and distal ends, the proximal end being coupled to the cartridge arm at a pivot point, the anvil in a torqued configuration when a plurality of staples are driven from the cartridge arm and deformed against the anvil, and being in a non-torqued configuration when no staples are driven against the anvil; and
    a support coupled to the anvil and moveable between a proximal position and distal position, the support adapted to contact the anvil at a location distal to the pivot point to reduce deflection of the anvil in the torqued configuration relative to the non-torqued configuration, the support in the distal position
        (i) contacting at least a portion of the anvil at a location closer to the distal end of the anvil relative to when the support is in the proximal position, and,
        (ii) urging the anvil and cartridge arm toward a closed position.

9. The surgical stapler of claim 8, wherein the support in the proximal position allows the anvil to move about the pivot point, and the support in the distal position preventing the anvil from moving about the pivot point.

10. The surgical stapler of claim 8, wherein the support includes at least two linkages pivotally coupled to one another, at least one of the linkages being slidably coupled to the anvil.

11. The surgical stapler of claim 8, wherein the support comprises:
    a distal linkage slidably coupled to the anvil;
    a proximal linkage pivotally coupled at one end to the distal linkage and at an opposite end to an elongate shaft extending proximally from the cartridge arm; and
    a middle linkage pivotally coupled at one end to the elongate shaft and pivotally coupled at an opposite end to the distal linkage and the proximal linkage.

12. The surgical stapler of claim 8, further comprising a stop adapted to limit distal movement of the support relative to the anvil.

13. The surgical stapler of claim 12, wherein the stop comprises an elongate slot formed in the anvil, and a pin member coupled to the support and slidably disposed in the elongate slot.

14. The surgical stapler of claim 13, wherein the elongate slot in the anvil terminates proximal to the distal end of the anvil.

15. The surgical stapler of claim 8, wherein the cartridge arm includes a staple cartridge disposed therein and containing a plurality of staples arranged in at least one linear row.

16. The surgical stapler of claim 8, wherein the cartridge arm and anvil have a length of at least about 60 mm.

17. The surgical stapler of claim 8, wherein the cartridge arm and anvil have a length of at least about 90 mm.

18. The surgical stapler of claim 9, wherein the cartridge arm, anvil, and support have a maximum outer diameter of less than about 16 mm when the support is in the proximal position.

19. The surgical stapler of claim 1, wherein the end effector and the support are adapted to be utilized in at least one of an endoscopic procedure and a laparoscopic procedure.

20. The surgical stapler of claim 1, wherein the end effector is adapted to engage tissue when the distal end of the support is in the proximal-most position and the distal-most position.

21. The surgical stapler of claim 8, wherein the cartridge arm and the anvil are adapted to be utilized in at least one of an endoscopic procedure and a laparoscopic procedure.

22. The surgical stapler of claim 8, wherein the cartridge arm and the anvil are adapted to engage tissue when the support is in the proximal position and the distal position.

23. The surgical stapler of claim 1, wherein the distal end of the support in the proximal-most position engages a more proximal position on the anvil relative to when the distal end of the support is in the distal-most position.

24. The surgical stapler of claim 1, wherein the cartridge arm and the anvil define a length of the end effector that is effective to drive staples into tissue and the support is adapted to contact a mid-portion of the length of the end effector that is effective to drive staples into tissue.

25. The surgical stapler of claim 9, wherein a length of the anvil is adapted to receive and form staples driven by the cartridge arm and the support is adapted to contact a portion of the length to reduce deflection of the anvil.

* * * * *